(12) United States Patent
Flohr et al.

(10) Patent No.: US 8,553,833 B2
(45) Date of Patent: Oct. 8, 2013

(54) X-RAY IMAGING METHOD AND APPARATUS TO REDUCE X-RAY EXPOSURE OF SUBJECT REGIONS OTHER THAN THE DIAGNOSTICALLY RELEVANT SUBJECT REGION

(75) Inventors: Thomas Flohr, Uehlfeld (DE); Michael Grasruck, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 5 days.

(21) Appl. No.: 13/447,524

(22) Filed: Apr. 16, 2012

(65) Prior Publication Data

US 2012/0263272 A1    Oct. 18, 2012

(30) Foreign Application Priority Data

Apr. 15, 2011   (DE) .......................... 10 2011 007 535

(51) Int. Cl.
*G01N 23/04* (2006.01)
(52) U.S. Cl.
USPC .......................................................... 378/15
(58) Field of Classification Search
USPC .......................................... 378/4, 19, 15, 62
See application file for complete search history.

(56) References Cited

U.S. PATENT DOCUMENTS

| | | |
|---|---|---|
| 4,998,268 A | 3/1991 | Winter |
| 6,327,326 B1 | 12/2001 | Flohr et al. |
| 6,445,761 B1 | 9/2002 | Miyazaki et al. |
| 7,466,792 B2 | 12/2008 | Bakai et al. |
| 2002/0172321 A1* | 11/2002 | Sembritzki et al. ............... 378/8 |
| 2010/0067647 A1 | 3/2010 | Bani-Hashemi et al. |
| 2010/0254508 A1 | 10/2010 | Von Der Haar |

* cited by examiner

*Primary Examiner* — Irakli Kiknadze
(74) *Attorney, Agent, or Firm* — Schiff Hardin LLP

(57) ABSTRACT

In a method for operating an imaging apparatus, and an imaging apparatus that has an x-ray source with a focus and a measurement volume with a central axis around which measurement volume the focus can be moved, acquisition of x-ray projections of a measurement subject that is arranged eccentrically relative to the central axis in the measurement volume are produced. The segment of the measurement volume in which the measurement subject is arranged is established based on an overview image and the projection angle range $\Delta\alpha$ in which x-ray projections should only be acquired in order to be able to reconstruct at least one image of the measurement subject is determined based on the establishment of the segment of the measurement volume.

11 Claims, 3 Drawing Sheets

X-RAY IMAGING METHOD AND APPARATUS TO REDUCE X-RAY EXPOSURE OF SUBJECT REGIONS OTHER THAN THE DIAGNOSTICALLY RELEVANT SUBJECT REGION

BACKGROUND OF THE INVENTION

1. Field of the Invention

The present invention concerns a method for operating an x-ray imaging apparatus, and an imaging apparatus that has an x-ray source having a focus and a measurement volume with a central axis around which the focus can be moved. The method is provided to acquire x-ray projections of a measurement subject that is arranged eccentrically relative to the central axis in the measurement volume.

The present invention also concerns a non-transitory data storage medium encoded with programming instructions to implement such a method.

2. Description of the Prior Art

In the acquisition of x-ray projections of a measurement subject to reconstruct at least one image of the measurement subject, particularly in computed tomography, situations can arise in which the measurement subject cannot be arranged in the isocenter of the computed tomography apparatus, i.e., such that the central axis of the measurement volume of the computer tomography apparatus runs through the measurement subject. An example is the examination of a female breast (for radiation therapy planning, for example) that is supported eccentrically relative to the central axis. The challenge in the examination of the female breast is to expose the other body parts of the patient that are not to be examined (for example the other breast of the patient) to as little x-ray radiation as possible.

A known response to this problem is a general reduction of the radiation dose during the acquisition of the x-ray projections, for example by reducing the tube current of the x-ray tube, but this entails the disadvantage of a (normally) reduced image quality of the reconstructed images. Furthermore, body parts that are to be protected are sometimes covered with radiation-absorbing mats, which have the disadvantage of increased image artifacts in the reconstructed images. In the case of a female breast, items known as "breast shields" were and are used. Moreover, an optimally good centering of the body part to be examined in the measurement volume of the computed tomography apparatus always has been and is sought, but this is not always possible due to the dimensions of the patient or of the inside of the patient, and the limited size of the opening of the gantry of the computed tomography apparatus.

SUMMARY OF THE INVENTION

An object of the invention is to provide a method, an imaging medical apparatus and a data storage medium of the aforementioned type wherein, in the examination of a measurement subject that is supported eccentrically in a measurement volume, parts of the measurement subject are exposed to as little x-ray radiation as possible.

According to the invention, this object is achieved by a method for operating an x-ray imaging apparatus that has an x-ray source with a focus and that has measurement volume with a central axis, around which measurement volume the focus can be moved, for the acquisition of x-ray projections of a measurement subject that is arranged eccentrically relative to the central axis in the measurement volume. In the method, the segment of the measurement volume in which the measurement subject is arranged is established based on an overview image including the measurement subject (preferably an overview image slice image including the measurement subject). The projection angle range $\Delta\alpha$ in which x-ray projections should or must only be acquired in order to be able to reconstruct at least one image of the measurement subject is determined based on the establishment of the segment of the measurement volume.

The goal of the method is thus to determine the projection angle interval or range $\Delta\alpha$ (namely the range in which x-ray projections of the measurement subject should be acquired per revolution of the focus around the measurement subject in order to reconstruct at least one image of the measurement subject) for a measurement subject supported eccentrically relative to the central axis of the measurement volume (based on the identification of the segment in which the measurement subject is arranged), such that other parts of the measurement subject—for example other than the body part of the patient that is to be examined, receive as little x-ray radiation as possible. According to the method, the projection angle interval $\Delta\alpha$ necessary for the acquisition of x-ray projections is virtually minimized.

As noted, the identification or establishment of the segment of the measurement volume in which the measurement subject is arranged preferably takes place on the basis of an overview slice image including the measurement subject. This overview slice image can be generated with the imaging apparatus (for example a computed tomography apparatus) itself, or can also be generated with a different imaging apparatus, for example an ultrasound apparatus or a magnetic resonance apparatus.

According to an embodiment of the invention, the segment of the measurement volume is established in that the image section in which the measurement subject is separated in the overview image or in the overview slice image by means of a straight line from the remainder of the overview slice image. The entry of the straight line takes place such that optimally only the measurement subject is included as completely as possible in the image section, wherein the image section is at the same time chosen to be as small as possible. With regard to the measurement volume, the straight line can be expanded in the directions of the central axis relative to a slice plane, such that the segment of the measurement volume is also established. The establishment is normally conducted by a user or operator of the method who can conduct the establishment or the plotting of the straight line, for example at a graphical user interface of a computer of the imaging apparatus.

According to a further embodiment of the invention, to determine the projection angle range $\Delta\alpha$ the focus of the x-ray source at least virtually assumes that projection angle $\alpha 1$ in the plane of the overview slice image in which the straight line runs through the focus of the x-ray source of the imaging apparatus, and that forms the first projection angle of the projection angle range $\Delta\alpha$ under consideration of the rotation direction of the focus. Since the overview image or the overview slice image and the measurement volume are linked with one another, the focus can at least virtually assume the projection angle $\alpha 1$ in the plane of the overview image or of the overview slice image.

According to another embodiment of the invention, a Cartesian coordinate system is associated with the imaging apparatus (and thus also with the overview image or the overview slice image), wherein the central axis of the measurement volume corresponds to the z-axis of the coordinate system, and wherein the straight line established in the overview image or the overview slice image is unambiguously established by its distance A from the z-axis in the direction of gravity to the z-axis in the plane of the overview slice image, and by at least one angle that includes the plumb line with one of the additional coordinate axes. For the establishment of the straight line, the angle θ is preferably taken into account that encloses the plumb line with the y-axis of the Cartesian coordinate system in the plane of the overview slice image.

According to a further embodiment of the invention, the last projection angle $\alpha_2$ of the projection angle range $\Delta\alpha$ in the plane of the overview slice image is calculated as follows:

$$\alpha_2 = \alpha_1 + \pi - 2\gamma$$

wherein $$\alpha_1 = \theta - \gamma \text{ and } \gamma = \arcsin(A/R_F)$$

with

θ, the angle that encloses the plumb line with the additional coordinate axis;

γr, the angle that encloses the straight line with the central ray of the x-ray beam that travels through the focus and the central axis when the focus assumes the projection angle $\alpha_1$;

$R_F$, the distance of the focus from the central axis.

A "central ray" of an x-ray beam (in particular a fan-shaped or pyramidal x-ray beam) means the middle ray of the x-ray beam that travels through the central axis. The distance $R_F$ is established by the dimensions of the imaging apparatus.

Overall, x-ray projections are accordingly acquired only in the projection angle range $\Delta\alpha = \pi - 2\gamma$ in each revolution of the focus around the measurement volume. The projection angle range can be at most π when the straight line travels through the central axis or, respectively, the z-axis.

To further reduce the radiation exposure, in a further embodiment of the invention the aperture width and the position of a radiation window of a diaphragm associated with the x-ray source in the direction of the fan angle β of an x-ray projection are set dynamically depending on the respective projection angle α, as considered for each x-ray projection, during the acquisition of x-ray projections of the measurement subject in the projection angle range $\Delta\alpha$. The aperture width and the position of the radiation window are respectively set such that optimally only the measurement subject is permeated with x-ray radiation in each x-ray projection. The basis for the respective setting of the aperture width and the position of the radiation window for each projection angle α of the projection angle range $\Delta\alpha$ can in turn be the overview slice image exhibiting the measurement subject.

The object of the invention is also achieved by an imaging apparatus having a computer that executes a computer program that implants one or more of the embodiments of the method described above. The imaging apparatus can be a diagnostic computed tomography apparatus or a radiation therapy apparatus that has a diagnostic x-ray acquisition system that includes an x-ray source and an x-ray detector.

The above object also is achieved in accordance with the invention by a non-transitory, computer-readable data storage medium that, when loaded into a computerized control and evaluation unit of an x-ray imaging system causes one or more of the embodiments of the above-described method to be implemented by programming instructions that are encoded on the data storage medium.

The object of the invention also is achieved by a method as described above that is implemented to acquire at least one image data set of a measurement subject with an imaging apparatus for the planning of a radiation therapy in the measurement subject, in order to keep the radiation dose exposure a low as possible for parts of the measurement subject that are situated outside of the segment of the measurement volume, or to acquire an image data set of the measurement subject during the implementation of a radiation therapy.

DESCRIPTION OF THE PREFERRED EMBODIMENTS

Figure 1:
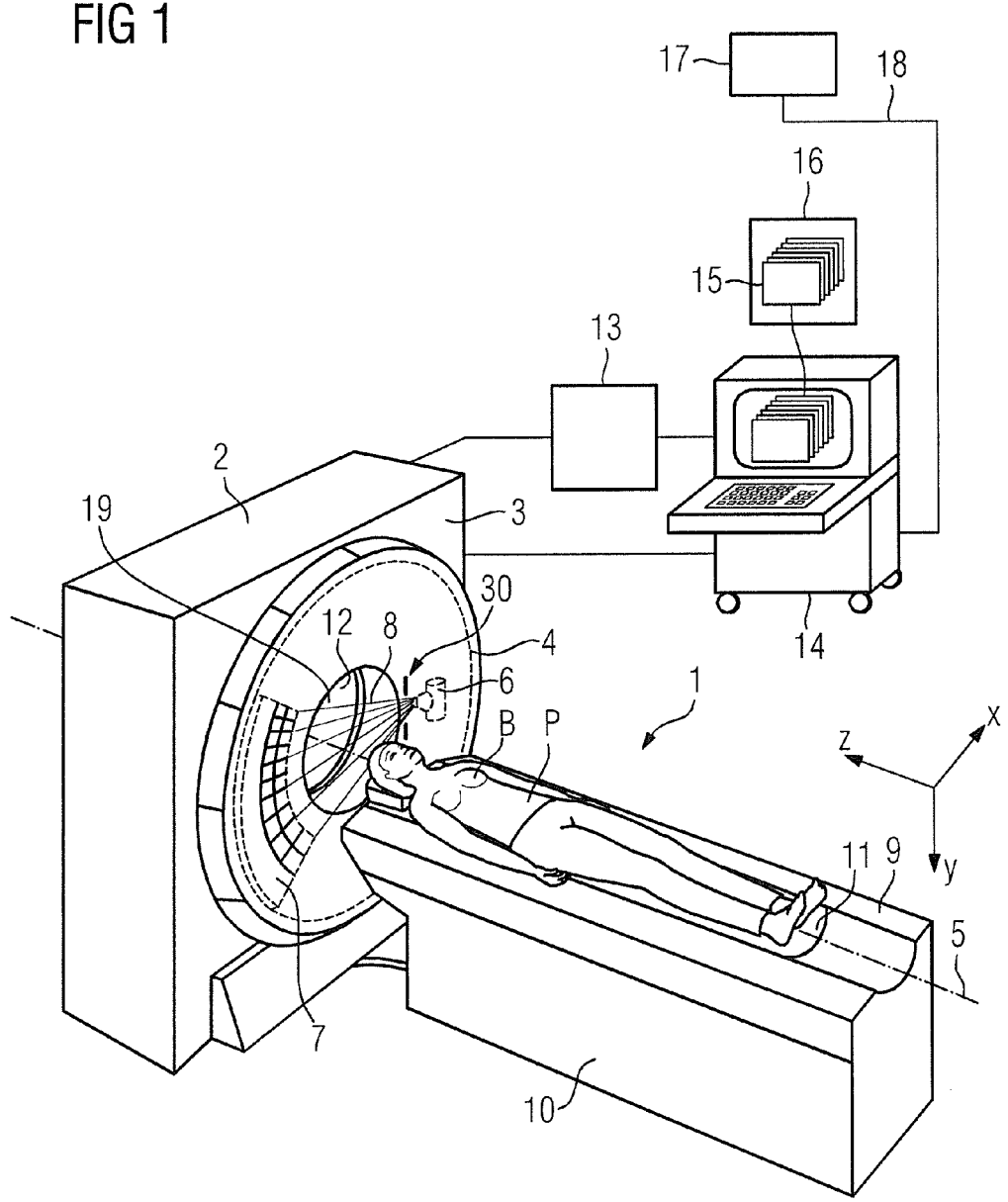
FIG. 1 shows a computed tomography apparatus according to the invention.

Identical or functionally identical elements are consistently provided with identical reference characters in Figures. The representations in Figures are schematic and not necessarily true to scale. In the exemplary embodiment of the invention, the imaging apparatus is a computed tomography apparatus that is discussed in the following (and without limitation of the generality) of the invention.

The computed tomography apparatus 1 shown in FIG. 1 has a gantry 2 with a stationary part 3 and with a part 4 that is rotatable around a system axis 5. In the exemplary embodiment of the invention, the rotatable part 4 has an x-ray system that includes an x-ray tube 6 and an x-ray detector 7 that are arranged opposite one another on the rotatable part 4. In the operation of the computed tomography apparatus 1, x-ray radiation 8 emanates from the x-ray tube 6 in the direction of the x-ray detector 7, penetrates a measurement subject, and is detected by the x-ray detector 7 in the form of measurement data or measurement signals. The x-ray detector 7 establishes a cylindrical measurement volume 19 having a central axis in the opening 12 of the gantry 2, defined by its extent in the direction of the system axis 5 as well as by rotation around the system axis 5. The system axis 5 coincides with the central axis of the measurement volume 19.

The computed tomography apparatus 1 furthermore has a patient bed 9 to support a patient P to be examined. The patient bed 9 has a bed base 10 on which is arranged a patient support plate 11 provided to actually support the patient P. The patient support plate 11 can be displaced relative to the bed base 10 in the direction of the system axis 5 such that it, together with the patient P, can be introduced into the opening 12 and thus into the measurement volume 19 of the gantry 2 in order to acquire 2D x-ray projections of the patient P, for example in a spiral scan.

The computational processing of the 2D x-ray projections acquired with the x-ray system or the reconstruction of slice images, 3D images or a 3D image data set based on the measurement data or the measurement signals of the 2D x-ray projections takes place with an image computer 13 (schematically depicted) of the computed tomography apparatus 1.

The computed tomography apparatus 1 also has a computer 14 with a display device. With the computer 14, computer programs can be and are executed for the operation and control of the computer tomography apparatus 1. The computer 14 does not need to be fashioned as a separate computer 14, rather, it can also be integrated into the computed tomography apparatus 1.

In the exemplary embodiment of the invention, a computer program 15 that implements the method according to the invention for the acquisition of x-ray projections of an eccentrically borne measurement subject is loaded into the computer 14. The computer program 15 represents a special operating mode for the computed tomography apparatus 1 and can have been loaded into the computer 14 from a portable data medium (for example from a CD 16 or from a memory stick) or from a server 17 via a network 18, which can be a public network or also a network internal to a clinic or hospital.

Figure 2:
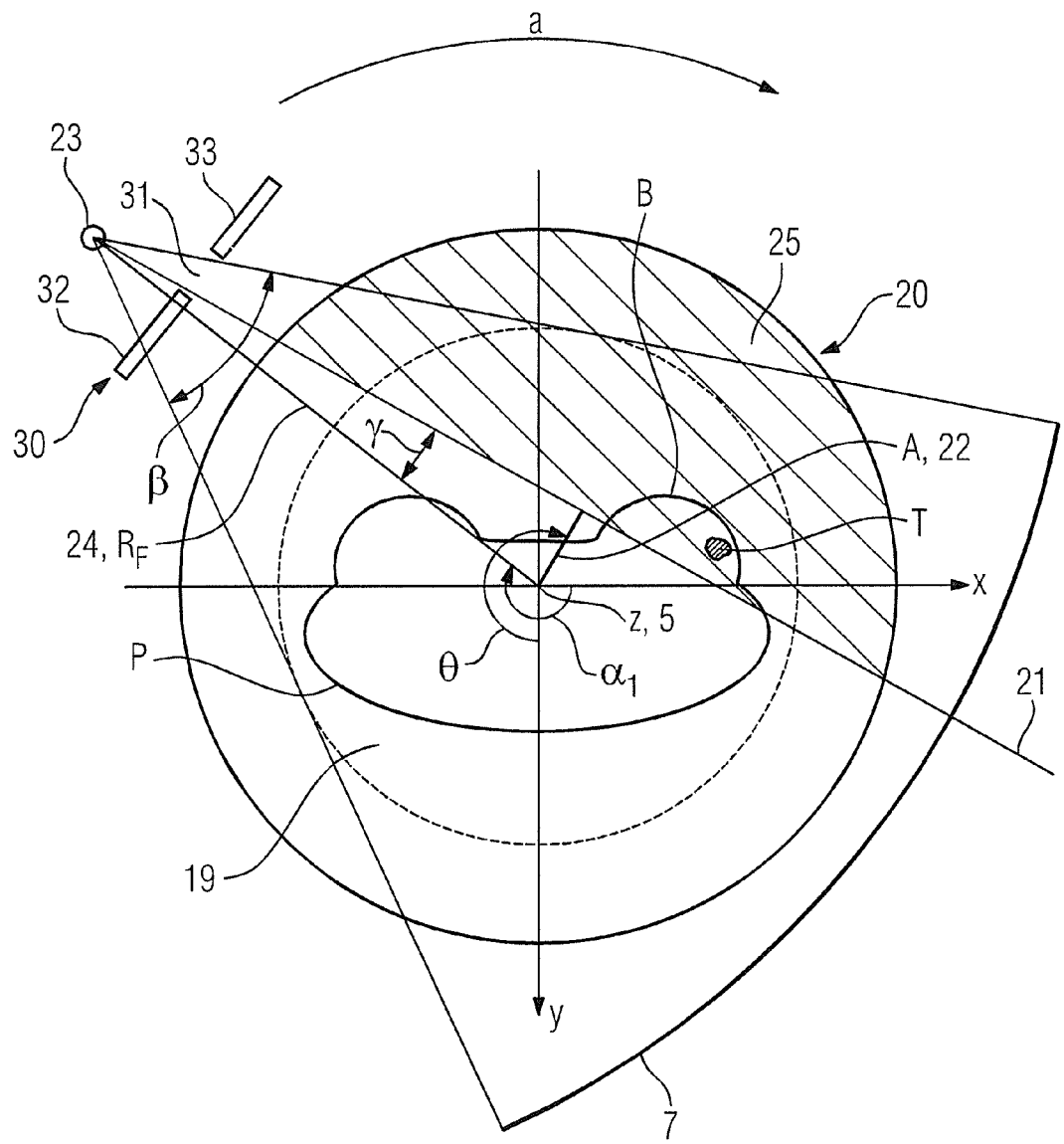
FIG. 2 and FIG. 3 illustrate the determination of the projection angle range $\Delta\alpha$ in accordance with the invention.

In the exemplary embodiment of the invention, the method according to the invention is used to plan a radiation therapy of a tumor T in the left breast B of a patient P. For this purpose, in the exemplary embodiment of the invention an overview image or an overview slice image of the body region of the patient P that includes the left breast B is initially generated with the computer tomography apparatus 1. FIG. 2 schematically shows the overview slice image 20, which is displayed on the display device of the computer 14 (in a graphical user interface, for example) for the further procedure. Moreover, the focus 23 of the x-ray tube 6 and the x-ray detector 7 of the computed tomography apparatus 1 are symbolically drawn in FIG. 2 only for the additional explanation of the method.

A Cartesian coordinate system with an x-axis and a y-axis is associated with the overview slice image 20. The z-axis is situated perpendicularly to the plane of the paper and travels into the plane of the paper. The axes of the Cartesian coordinate system of the overview slice image 20 have their counterpart in the computer tomography apparatus 1. Most obvious is the correlation of the z-axis of the coordinate system with the system axis 5 of the computer tomography apparatus 1, which is also the central axis of the computer tomography apparatus 1 or of the cylindrical measurement volume 19 of the computer tomography apparatus 1.

Moreover, the overview slice image 20 does not necessarily need to be generated with the computed tomography apparatus 1. Rather, the overview slice image 20 can also be generated with another imaging apparatus, for example an ultrasound apparatus or a magnetic resonance apparatus. In this case, however, a registration with the computed tomography apparatus 1 or with its image coordinate system must take place to the effect that an unambiguous relationship is established between the coordinate system of the overview slice image and the image coordinate system of the computed tomography apparatus 1, and thus with the coordinate system of the computed tomography apparatus 1.

As can be seen from the overview slice image 20 of FIG. 2, the left breast B of the patient P (which, in the case of the present exemplary embodiment of the invention, is the measurement subject) is not supported centrally such that the central axis 5 or the z-axis travels through the left breast B of the patient P. Due to the dimensions of the computed tomography apparatus 1, in particular the opening 12 of the gantry 2 and the limited positioning possibilities of the patient bearing plate 11, the left breast B of the patient P is arranged eccentrically with regard to the central axis 5, which is the z-axis in the measurement volume 19 of the computed tomography apparatus 1.

In order to charge the other body parts of the patient P (for example the right breast of said patient P) with as little x-ray radiation as possible in the acquisitions of x-ray projections of the left breast B of said patient P that are necessary within the scope of planning the radiation therapy, in the method according to the invention the segment of the measurement volume 19 in which the left breast is arranged is initially established. For this purpose, in the overview slice image 20 a straight line 21 is plotted such that the image section 25 exhibiting the left breast B is separated from the remainder of the overview slice image 20. The body part of the patient P that is to be examined—thus the left breast B—lies in the hatched image section 25. The plotting of the straight line 21 is conducted by a user, wherein the plotting takes place via the graphical user interface (in which said straight line 21 is established with a computer mouse, for example). If the straight line 21 is extended in the directions of the central axis 5 or, respectively, the z-axis, a slice plane is created that establishes the segment of the measurement volume 19 in which the left breast B is arranged.

Based on the establishment of the segment of the measurement volume 19 or, respectively, based on the establishment of the straight line 21, the projection angle range $\Delta\alpha$ in the plane of the overview slice image 20 is determined in which (and in fact only in which) x-ray projections should be acquired for the reconstruction of at least one image of the left breast B.

The straight line 21 is unambiguously established in the plane of the overview slice image 20 or, respectively, in the Cartesian coordinate system by its distance A from the z-axis, which corresponds to the central axis 5 of the measurement volume 19 in the direction of its plumb line 22 to the z-axis, and by the angle $\theta$ that encloses the plumb line 22 with the positive y-axis.

As is shown in FIG. 2, for the further determination of the projection angle range $\Delta\alpha$ the focus 23 of the x-ray tube 6 at least virtually assumes that projection angle $\alpha1$ relative to the x-axis in the plane of the overview slice image 20 at which the straight line 21 travels through the focus 23 and that, under consideration of the rotation direction of the focus 23 (see arrow a in FIG. 2), forms the first projection angle of the projection angle range $\Delta\alpha$. The first projection angle $\alpha1$ of the projection angle range $\Delta\alpha$ is established in this manner. The central ray 24 of the x-ray beam 8 belonging to the projection angle $\alpha1$ thereby travels through the z-axis, (the central axis 5) in the plane of the overview slice image.

Figure 3:
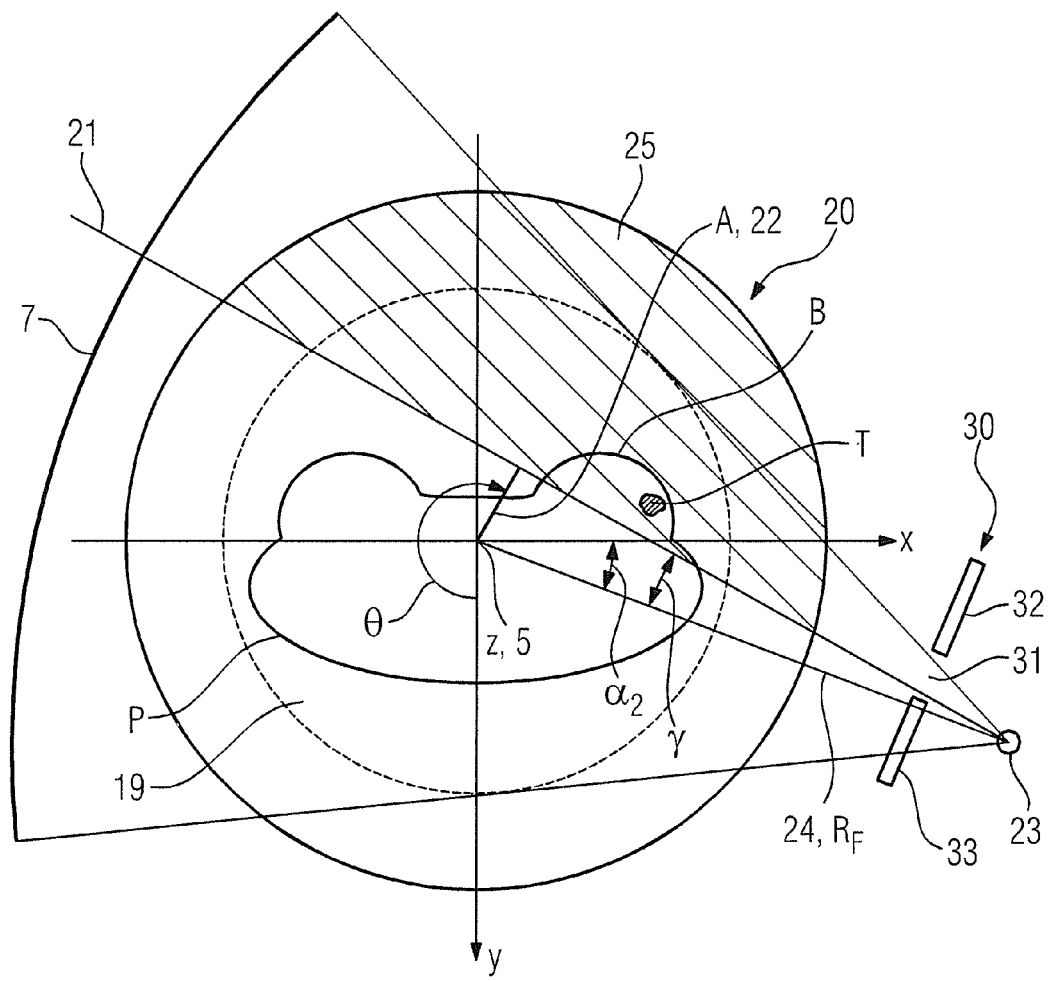

The last projection angle $\alpha_2$ of the projection angle range $\Delta\alpha$ can then be determined as follows under consideration of the situations (illustrated in FIGS. 2 and 3) in the plane of the overview slice image 20:

$$\alpha_2 = \alpha_1 + \pi - 2\gamma$$

wherein $$\alpha_1 = \theta - \gamma \text{ and } \gamma = \arcsin(A/R_F)$$

with $\theta$, the angle that encloses the plumb line 22 with the positive y-axis;

$\gamma$, the angle that encloses the straight line 21 with the central ray 24 of the x-ray beam 8 that travels through the focus 23 and the z-axis when the focus 23 assumes the projection angle $\alpha1$ in the plane of the overview slice image 20;

$R_F$, the distance of the focus from the central axis.

The projection angle range $\Delta\alpha = \alpha_2 - \alpha_1$ is determined in this manner in that x-ray projections of the left breast B of the patient P are acquired in the plane of the overview slice image 20 (and possibly each plane parallel to this) per rotation of the focus 23 around the system or central axis 5.

In order to further decrease the radiation exposure for other body parts of the patient P in the acquisition of x-ray projections of the left breast B, in the case of the present exemplary embodiment of the invention a diaphragm 30 with a dynamically adjustable radiation window 31 is also associated with the x-ray tube 6. The aperture width and the position of the radiation window 31 of the diaphragm 30 can be dynamically adjusted with diaphragm leaves 32, 33 of the diaphragm 30 in the direction of the fan angle $\beta$ of a beam fan of the x-ray beam 8, as considered for each x-ray projection depending on the respective projection angle $\alpha$ of the projection angle range $\Delta\alpha$.

The aperture width and the position of the beam window are respectively set such that optimally only the left breast B of the patient is permeated by x-ray radiation. In the case of the present exemplary embodiment of the invention, the basis of the respective adjustment of the aperture width and the position of the radiation window 31 for each projection angle α of the projection angle range Δα is the overview slice image 20 exhibiting the measurement subject.

Projections that are possibly truncated in the direction of the fan angle β can be supplemented via data from a data extrapolation method.

The inventive method also achieves the result that x-ray radiation does not enter into the body of the patient P through the skin surface of the body parts of said patient P that are located outside of the established segment of the measurement volume, so the skin dose of x-ray radiation applied to the patient P is reduced.

Instead of the diagnostic computed tomography apparatus, the imaging apparatus can also be an apparatus that has a therapeutic x-ray source for radiation therapy and a diagnostic x-ray acquisition system with a diagnostic x-ray source and with an x-ray detector. The therapeutic x-ray source and the diagnostic x-ray source differ with regard to the energy of the x-ray radiation that they emit. The photon energy of therapeutic x-ray radiation is in the MeV range, and the photon energy of diagnostic x-ray radiation is in the keV range. The diagnostic x-ray acquisition system is advantageously arranged like a diagnostic computer tomography apparatus on a rotatable part of a gantry (see FIG. 1).

Given use of such an apparatus, the method according to the invention can also be used to acquire one or more image data sets of the measurement subject with the diagnostic x-ray acquisition system during the implementation of a radiation therapy with the therapeutic x-ray source, for example in order to track the therapy.

The method according to the invention is moreover not limited to the use for therapy planning or in therapy; rather, it can be used only for diagnostic purposes.

Furthermore, the measurement subject does not necessarily need to be a breast. For example, the measurement subject can also be an arm, a leg etc.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for operating an imaging apparatus comprising an x-ray source with a focus from which an x-ray beam is emitted, and a measurement volume comprising a central axis, said method comprising:
   placing an examination subject in said measurement volume, said examination subject comprising a measurement object, of which an image is to be obtained, that is located eccentrically relative to said central axis;
   generating an overview image of said examination subject in said measurement volume and, in a processor, automatically identifying a portion of the measurement volume in which said measurement object is located;
   in said processor, dependent on the identified portion of the measurement volume in which the measurement object is located, automatically determining a projection angle range to which acquisition of only a number of x-ray projections will be confined, with said number of x-ray projections being sufficient to reconstruct at least one image of the measurement object;
   rotating at least said focus of said x-ray source around said measurement volume through said projection angle range to acquire said number of x-ray projections of said measurement object; and
   in a computer, reconstructing said at least one image of the measurement object from said number of x-ray projections.

2. A method as claimed in claim 1 comprising forming said processor and said computer as a single computerized component.

3. A method as claimed in claim 1 comprising, in said processor, defining said portion of said measurement volume in which said measurement object is located by establishing a straight line through said measurement volume in said overview image, said straight line separating said portion of said measurement volume is located from a remainder of said measurement volume.

4. A method as claimed in claim 3 comprising, in said processor, associating a Cartesian coordinate system with said imaging apparatus and thus also with said overview image, with said central axis of said measurement volume corresponding to the z-axis of said Cartesian coordinate system, and establishing said straight line in said overview image by a distance thereof from said z-axis in a direction of a plumb line from said straight line to said z-axis, and by at least one angle that is formed by said plumb line with one of the y-axis or the x-axis of said Cartesian coordinate system.

5. A method as claimed in claim 3 comprising, in said processor, determining said projection angle range by implementing an algorithm wherein said focus of said x-ray source assumes a projection angle at which said straight line proceeds through said focus, and using said projection angle at which said straight line proceeds through said focus as a first projection angle of said projection angle range, with respect to a rotation direction of said focus around said measurement volume.

6. A method as claimed in claim 5 comprising, in said processor, associating a Cartesian coordinate system with said imaging apparatus and thus also with said overview image, with said central axis of said measurement volume corresponding to the z-axis of said Cartesian coordinate system, and establishing said straight line in said overview image by a distance thereof from said z-axis in a direction of a plumb line from said straight line to said z-axis, and by at least one angle that is formed by said plumb line with one of the y-axis or the x-axis of said Cartesian coordinate system.

7. A method as claimed in claim 6 comprising, in said processor, determining said projection angle range as a projection angle range that has a last projection angle $\alpha_2$, with respect to a direction of rotation of said focus around said measurement volume, with $$\alpha_2 = \alpha_1 + \pi - 2\gamma$$

wherein $\alpha_1$ is said first projection angle and $$\alpha_1 = \theta - \gamma \text{ and } \gamma = \arcsin(A/R_F)$$

with
   θ is the angle formed by the plumb line with said one of said y-axis or said x-axis,
   γ is the angle formed by the straight line with the central ray of the x-ray beam that travels through the focus and the central axis when the focus assumes the projection angle $\alpha_1$, and
   $R_F$ is a distance of the focus from the central axis.

8. A method as claimed in claim 1 comprising limiting said x-ray beam with a diaphragm associated with said x-ray source by setting an aperture width of a radiation-passage window of said diaphragm in a direction of a fan angle of an x-ray projection dynamically dependent on the respective projection angle currently assumed by said focus for each x-ray projection, during acquisition of said x-ray projections in said projection angle range.

9. A method as claimed in claim 8 comprising setting said aperture width and position of said radiation-passage window respectively to cause substantially only said measurement object to be irradiated with said x-ray radiation.

10. An x-ray imaging apparatus comprising;
- an x-ray source with a focus from which an x-ray beam is emitted into a measurement volume comprising a central axis;
- a support configured to support an examination subject in said measurement volume, said examination subject comprising a measurement object, of which an image is to be obtained, that is located eccentrically relative to said central axis;
- a processor provided with an overview image of said examination subject in said measurement volume, said processor being configured to automatically identify a portion of the measurement volume in which said measurement object is located;
- said processor being configured to determine, dependent on the identified portion of the measurement volume in which the measurement object is located, a projection angle range to which acquisition of only a number of x-ray projections will be confined, with said number of x-ray projections being sufficient to reconstruct at least one image of the measurement object;
- a control unit configured to operate said x-ray source to rotate at least said focus of said x-ray source around said measurement volume through said projection angle range to acquire said number of x-ray projections of said measurement object; and
- a computer configured to reconstruct said at least one image of the measurement object from said number of x-ray projections.

11. A non-transitory, computer-readable data storage medium encoded with programming instructions, said storage medium being loaded into a computerized control and processing system of an imaging apparatus that comprises an x-ray source having a focus from which an x-ray beam is emitted into a measurement volume comprising a central axis, with an examination subject being located in said measurement volume, said examination subject comprising a measurement object, of which an image is to be obtained, located eccentrically relative to said central axis of said measurement volume, said programming instructions causing said computerized control and evaluation system to:
- use an overview image of said examination subject in said measurement volume to automatically identify a portion of the measurement volume in which said measurement object is located;
- dependent on the identified portion of the measurement volume in which the measurement object is located, determine a projection angle range to which acquisition of only a number of x-ray projections will be confined and in which said number of x-ray projections is sufficient to reconstruct at least one image of the measurement object;
- operate said x-ray source to rotate at least said focus of said x-ray source around said measurement volume through said projection angle range to acquire said number of x-ray projections of said measurement object; and
- reconstruct said at least one image of the measurement object from said number of x-ray projections.

* * * * *